(12) United States Patent
Vingron et al.

(10) Patent No.: US 6,304,868 B1
(45) Date of Patent: Oct. 16, 2001

(54) METHOD FOR CLUSTERING SEQUENCES IN GROUPS

(75) Inventors: Martin Vingron; Antje Krause, both of Heidelberg (DE)

(73) Assignee: Deutsches Krebsforschungszentrum Stiftung des öff. Rechts, Heidelberg (DE)

( * ) Notice: Subject to any disclaimer, the term of this patent is extended or adjusted under 35 U.S.C. 154(b) by 0 days.

(21) Appl. No.: 09/529,018

(22) PCT Filed: Aug. 14, 1998

(86) PCT No.: PCT/DE98/02422

§ 371 Date: Jun. 16, 2000

§ 102(e) Date: Jun. 16, 2000

(87) PCT Pub. No.: WO99/21107

PCT Pub. Date: Apr. 29, 1999

(30) Foreign Application Priority Data

Oct. 17, 1997 (DE) .............................................. 197 45 665

(51) Int. Cl.[7] ..................................................... G06F 17/00
(52) U.S. Cl. .................................. 707/2; 702/20; 707/10; 707/104; 707/204
(58) Field of Search ................................. 712/20; 707/2, 707/10, 104, 204

(56) References Cited

FOREIGN PATENT DOCUMENTS 0 646 883  9/1994  (EP) .
0 742 525  4/1996  (EP) .

OTHER PUBLICATIONS

Murzin et al. Distant homology recognition using structural classification of proteins. Proteins, Suppl. 1, pp.105–112, 1997.*
Altschul et al. Gapped BLAST and PSI–BLAST: a new geneeration of protein database search programs. Nucleic Acids Research, Vol. 25(7), pp. 3389–3402, (Sep. 1, 1997).*
Pearson et al. Improved tools for biological sequence comparison. Proc. Natl. Acad. Sci, Vol. 85(8), pp.2444–8 (1988).*
Harris et al. XP–002091600. "Class X: A Browsing Tool for Protein Sequence Megaclassifications" pp. 554–563 (1993). XP–002091665. Abstract. "Mega–Classification: discovering motifs in massive datastreams" . Harris et al. (1992).
Harris et al., N.L. et al., "ClassX: a browsing for protein sequence megaclassifications" PROCEEDING OF THE TWENTY–SIX HAWAII INTERNATIONAL CONFERENCE ON SYSTEM SCIENCES (CAT NO. 93TH0501–7), WAILEA, HI, USA, JAN 5–8. 1993, pp. 554–563, vol. 1, XP002091600 ISBN 8–8186–3230–5, 1993, Los Alamitos, CA, USA, IEEE, USA).

* cited by examiner

*Primary Examiner*—Marianne P. Allen
(74) *Attorney, Agent, or Firm*—Steven J. Hultquist; Marianne Fuierer

(57) ABSTRACT

In order to cluster sequences to biological groups, the conventional databank search programs are iteratively called in with a view to clustering various related sequences to one determined protein sequence. The inventive method enables full automatic distribution of a high number of protein sequences in groups. The major part of such groups are segregated, so that they represent a meaningful and valid grouping of data.

4 Claims, No Drawings

METHOD FOR CLUSTERING SEQUENCES IN GROUPS

This invention concerns a method of grouping sequences in families.

Large quantities of protein sequence data are generated today in molecular biology. A major problem here is how to group such protein sequence data logically in biological families. Since families are not defined exactly, but instead the diversity of different gene families varies, this involves a problem in data grouping which is not at all trivial.

In the past, biological information could only be of assistance for human experts who would thoroughly research the output of database searching programs and would create a grouping according to families. This method is time-consuming, labor-intensive and not very reproducible.

Therefore, the object of this invention is to find a method with which a large set of protein sequences can be divided into groups fully automatically.

This object is achieved with the features of Patent Claim 1.

The method described here is based on the finding that rapid grouping can be achieved when traditional database searching programs are run iteratively to find a quantity of sequences related to a given protein sequence.

It is advantageous if the method described here is carried out for each sequence in the database, removing clusters that occur repeatedly except for one cluster each, removing clusters that are contained in other clusters; of the remaining quantity of clusters, outputting the clusters that do not overlap with other clusters as partitioning of the database and outputting the remaining portion of the overlapping clusters as groups whose clusters are linked together by overlapping.

In this way, database clustering is achieved, resulting in the fact that most of the clusters are disjunctive to one another, and therefore a valid and reasonable clustering of data is achieved.

This method permits a much faster and more objective analysis of new sequence data than has been possible in the past. The paired disjunctive part of the clustering no longer requires any checking from a practical standpoint, and it forms the ideal basis for automatic annotations and more extensive analyses. The residue, i.e., the remaining portion of overlapping clusters, is the portion that must be studied by human experts. This portion is extremely reduced and is also prestructured due to the overlapping clusters.

This method can be carried out in an extremely short computation time because it is no longer necessary to compare each sequence separately with every other sequence in order to cluster an entire database.

In an advantageous embodiment, the threshold value is between $10^{-20}$ and $10^{-35}$. In practice, a value of $10^{-30}$ has proven feasible. In addition to clustering protein sequences, this method is also suitable for DNA sequences, where it may be appropriate to relax the threshold value beyond $10^{-20}$.

A further refinement of the method according to this invention consists of the fact that of the positive quantity of sequences found in one iteration step, not only the sequence weighted as worst, is used for another database search, but also all sequences of this quantity serve as a search sequence in additional searches. Due to the larger number of searches to be performed, this alternative is not as fast as the method described originally for an individual search. In conjunction with clustering, however, this does not cause any time loss.

However, since the sequence space around the initial sequence is searched more thoroughly, the resulting cluster has a high probability of already including all the sequences belonging to this protein family.

The "BLASTP" program is very suitable as a database searching program. This program is described in greater detail by S. F. Altschul, W. Gish, W. Miller, E. W. Myers, and D. J. Lipman, "Basic Local Alignment Search Tool," J. Mol. Biol., 215: 403–410, 1990.

As an alternative, however, the "FASTA" database search program may also be used as described, for example, in the following literature citation: W. R. Pearson and D. J. Lipman, "Improved tools for biological sequence comparison," Proc. Natl. Acad. Sci. USA, 85: 2444–2448, 1988.

In addition to the "BLASTP" and "FASTA" database search programs, any other database search program may also be used. For example, the "gapped BLAST" program (described by S. F. Altschul, T. L. Madden, A. A. Schaeffer, J. Zhang, Z. Zhang, W. Miller and D. J. Lipman, "Gapped BLAST and PSI-BLAST: a new generation of protein database search programs," Nucleic Acids Research, 25 (17): 3389–3402, 1997, is also suitable.

Using the "BLASTP" program, the PIR1 database, release 51, has been clustered by quantitative theory. This database contains 13,489 protein sequences and is described in detail by David G. George, Richard J. Dodson, John S. Garavelli, Daniel H. Haft, Lois T. Hunt, Christopher R. Marzee, Bruce C. Orcutt, Kathryn E. Sidman, Geetha Y. Srinivasarao, Lai-Su L. Yeh, Lieslie M. Arminski, Robert S. Ledley, Akira Tsugita and Winoma Barker, "The Protein Information Resource (PIR) and the PIR international protein sequence database," Nucleic Acids Research, 25 (1): 24–27, 1997. Grouping this database required approximately one day of computation time, and 91% of the database sequences were grouped into disjunctive clusters in a fully automatic procedure. The residue includes only approximately 9% of the database sequences.

The SWISS-PROT database, whose $34^{th}$ release contains 59,021 sequences, is a much larger database. This database is described by Amos Bairoch and Rolf Apweiler, "The SWISS-PROT protein sequence data bank and its supplement TrEMBL," Nucleic Acids Research, 25 (1):31–36, 1997. Within approximately five days of computation time, 80% of the sequences were classified in disjunctive classes.

These examples show that extreme savings in terms of computation time are possible with the method according to this invention in comparison with traditional methods, and the cluster results are excellent.

An algorithm for the method described here is presented below:

cluster←empty quantity
search sequence←inquiry sequence
as long as (search sequence defined)
    database searched with the search sequence
    positive quantity←all found sequences below the threshold level with a probability value
    search sequence←undefined
    if (first search) then
    reference quantity←positive quantity
    end if
    if (sequence exists in a positive quantity that is not contained in the cluster) and (intersecting quantity between the positive quantity and reference quantity is not blank)

then search sequence←sequence weighted as worst in the positive quantity not contained in the cluster cluster←combined quantity of cluster and positive quantity end if end as long as The sequence with which the search method begins is called the initial sequence, and the quantity of found sequences is called the cluster belonging to this initial sequence. First, a database search program such as "BLASTP" or "FASTA" is started with the initial sequence, and all sequences from the database that have a significant similarity with the initial sequence are accepted. We call this quantity of sequences a positive quantity, and we include it in the cluster as related sequences. There is a significant similarity between two sequences when the probability that this similarity occurs randomly is very low, i.e., below a given threshold. From the positive quantity thus obtained, we now use the sequence weighted as worst (i.e., the sequence having the highest probability) as a search sequence for another database search. This process is repeated as long as sequences below the threshold value are found which are not contained in the cluster and as long as there is an intersection quantity between the positive quantity of the initial sequence and the positive quantity of the instantaneous search sequence.

Then the following algorithm is carried out:

input: database output: partitioning of the database and groups with overlapping clusters perform the above database search method for all (sequences in the database)

cluster quantity←all clusters generated for all (identical clusters in the cluster quantity) remove identical clusters except for one representative cluster quantity←clusters without identical clusters for all (clusters in the cluster quantity contained completely in another cluster) remove the smaller cluster of this cluster pair cluster quantity←clusters without identical clusters and without inclusions partitioning←all clusters in the cluster quantity that do not overlap overlapping←all overlapping clusters in the cluster quantity are combined in groups To obtain database clustering, the method described above is carried out for all sequences in the database, i.e., each sequence is assigned a cluster of sequences to which it is related. From this quantity of clusters, all identical clusters are removed except for one example, because they do not contain any additional information. The remaining cluster quantity is then examined for inclusions, and clusters that are contained completely in other clusters are removed until no more inclusions are present. Of this cluster quantity, the clusters that do not overlap with others can now be regarded as a logical partitioning of the database. The remaining small number of overlapping clusters are combined in groups whose clusters are linked together among one another by overlapping.

An embodiment of this invention is described in greater detail below.

We use the sequence of the human homeobox engrailed-1 protein (HME1__HUMAN) as the inquiry sequence and then search the Swissprot database (release 34) with it for related sequences. The search is performed with the BLASTP program, and we select a threshold with a probability of $10^{-30}$. The result of this search looks approximately as follows (excerpts):

| Sequences found: | Probability: |
|---|---|
| SPR\|Q05925\|HME1__HUMAN HOMEOBOX PROTEIN ENGRAILED-1 (HU-E . . . | 2.4e-279 |
| SPR\|P09065\|HME1__MOUSE HOMEOBOX PROTEIN ENGRAILED-1 (MO-E . . . | 4.7e-189 |
| SPR\|Q05916\|HME1__CHICK HOMEOBOX PROTEIN ENGRAILED-1 (GG-E . . . | 4.6e-132 |
| SPR\|Q05917\|HME2__CHICK HOMEOBOX PROTEIN ENGRAILED-2 (GG-E . . . | 3.6e-95 |
| SPR\|P19622\|HME2__HUMAN HOMEOBOX PROTEIN ENGRAILED-2 (HU-E . . . | 8.0e-95 |
| SPR\|P09066\|HME2__MOUSE HOMEOBOX PROTEIN ENGRAILED-2 (MO-E . . . | 5.6e-92 |
| SPR\|P09015\|HME2__BRARE HOMEOBOX PROTEIN ENGRAILED-2 (ZF-E . . . | 5.2e-70 |
| SPR\|P31538\|HMEB__XENLA HOMEOBOX PROTEIN ENGRAILED-1B (EN- . . . | 1.5e-$\widehat{x}$ |
| SPR\|P52729\|HMEC__XENLA HOMEOBOX PROTEIN ENGRAILED-2A (EN- . . . | 2.1e-66 |
| SPR\|P52730\|HMED__XENLA HOMEOBOX PROTEIN ENGRAILED-2B (EN- . . . | 2.1e-65 |
| SPR\|P31533\|HME3__BRARE HOMEOBOX PROTEIN ENGRAILED-3 (ZF-E . . . | 6.1e-64 |
| SPR\|Q04896\|HME1__BRARE HOMEOBOX PROTEIN ENGRAILED-1 | 1.0e-61 |
| SPR\|P09145\|HMEN__DROVI SEGMENTATION POLARITY PROTEIN ENGR . . . | 9.1e-59 |
| SPR\|P05527\|HMIN__DROME INVECTED PROTEIN. | 4.5e-57 |
| SPR\|P27609\|HMEN__BOMMO SEGMENTATION POLARITY PROTEIN ENGR . . . | 1.5e-55 |
| SPR\|P27610\|HMIN__BOMMO INVECTED PROTEIN. | 1.1e-52 |
| SPR\|P09532\|HMEN__TRIGR HOMEOBOX PROTEIN ENGRAILED (SU-HB . . . | 4.0e-44 |
| SPR\|Q05640\|HMEN__ARTSF HOMEOBOX PROTEIN ENGRAILED. | 1.7e-42 |
| SPR\|P09076\|HME3__APIME HOMEOBOX PROTEIN E30 (FRAGMENT). | 2.1e-41 |
| SPR\|P09075\|HME6__APIME HOMEOBOX PROTEIN E60 (FRAGMENT). | 1.0e-40 |
| SPR\|P14150\|HMEN__SCHAM HOMEOBOX PROTEIN ENGRAILED (G-EN . . . | 2.3e-40 |
| SPR\|P23397\|HMEN__HELTR HOMEOBOX PROTEIN HT-EN (FRAGMENT). | 1.3e-38 |
| SPR\|P31537\|HMEA__XENLA HOMEOBOX PROTEIN ENGRAILED-1A (EN- . . . | 7.9e-33 |
| SPR\|P31535\|HMEA__MYXGL HOMEOBOX PROTEIN ENGRAILED-LIKE A . . . | 1.1e-27 |
| SPR\|P34326\|HM16__CAEEL HOMEOBOX PROTEIN ENGRAILED-LIKE CE . . . | 7.1e-27 |
| SPR\|P31536\|HMEB__MYXGL HOMEOBOX PROTEIN ENGRAILED-LIKE B . . . | 5.0e-26 |

On the basis of the threshold at $10^{-30}$, our cluster now contains the following sequences:

| | | | | |
|---|---|---|---|---|
| HME1_HUMAN, | HME1_MOUSE, | HME1_CHICK, | HME2_CHICK, | HME2_HUMAN, |
| HME2_MOUSE, | HME2_BRARE, | HMEB_XENLA, | HMEC_XENLA, | HMED_XENLA, |
| HME3_BRARE, | HME1_BRARE, | HMEN_DROVI, | HMIN_DROME, | HMEN_BOMMO, |
| HMEN_DROME, | HMIN_BOMMO, | HMEN_TRIGR, | HMEN_ARTSF, | HME3_APIME, |
| HME6_APIME, | HMEN_SCHAM, | HMEN_HELTR, | HMEA_XENLA. | |

The next run through the BLASTP program is then carried out with the sequence weighted as worst in this quantity, namely with the engrailed-1A homeobox protein of the horned toad (HMEA_XENLA). The result of this search looks as follows (excerpts):

| Sequences found: | Probability: |
|---|---|
| SPR\|P31538\|HMEB_XENLA HOMEOBOX PROTEIN ENGRAILED-1B (EN- . . . | 2.8e-36 |
| SPR\|P31537\|HMEA_XENLA HOMEOBOX PROTEIN ENGRAILED-1A (EN- . . . | 3.2e-36 |
| SPR\|P09015\|HME2_BRARE HOMEOBOX PROTEIN ENGRAILED-2 (ZF-E . . . | 1.1e-34 |
| SPR\|Q05925\|HME1_HUMAN HOMEOBOX PROTEIN ENGRAILED-1 (HU-E . . . | 1.3e-33 |
| SPR\|P09065\|HME1_MOUSE HOMEOBOX PROTEIN ENGRAILED-1 (MO-E . . . | 1.4e-33 |
| SPR\|Q05916\|HME1_CHICK HOMEOBOX PROTEIN ENGRAILED-1 (GG-E . . . | 1.5e-33 |
| SPR\|P52729\|HMEC_XENLA HOMEOBOX PROTEIN ENGRAILED-2A (EN- . . . | 9.9e-33 |
| SPR\|P52730\|HMED_XENLA HOMEOBOX PROTEIN ENGRAILED-2B (EN- . . . | 5.9e-32 |
| SPR\|Q05917\|HME2_CHICK HOMEOBOX PROTEIN ENGRAILED-2 (GG-E . . . | 1.3e-31 |
| SPR\|P09066\|HME2_MOUSE HOMEOBOX PROTEIN ENGRAILED-2 (MO-E . . . | 1.8e-31 |
| SPR\|P19622\|HME2_HUMAN HOMEOBOX PROTEIN ENGRAILED-2 (HU-E . . . | 2.0e-31 |
| SPR\|Q04896\|HME1_BRARE HOMEOBOX PROTEIN ENGRAILED-1. | 8.1e-31 |
| SPR\|P31535\|HMEA_MYXGL HOMEOBOX PROTEIN ENGRAILED-LIKE A . . . | 4.3e-30 |
| SPR\|P31533\|HME3_BRARE HOMEOBOX PROTEIN ENGRAILED-3 (ZF-E . . . | 6.7e-30 |
| SPR\|P31536\|HMEB_MYXGL HOMEOBOX PROTEIN ENGRAILED-LIKE B . . . | 1.8e-28 |
| SPR\|P09532\|HMEN_TRIGR HOMEOBOX PROTEIN ENGRAILED (SU-HB- . . . | 8.8e-28 |
| SPR\|P31534\|HMEN_LAMPL HOMEOBOX PROTEIN ENGRAILED-LIKE (E . . . | 8.8e-28 |
| SPR\|P09075\|HME6_APIME HOMEOBOX PROTEIN E60 (FRAGMENT). | 2.1e-26 |
| SPR\|P23397\|HMEN_HELTR HOMEOBOX PROTEIN HT-EN (FRAGMENT). | 2.3e-26 |
| SPR\|P09076\|HME3_APIME HOMEOBOX PROTEIN E30 (FRAGMENT). | 3.9e-26 |

This time we add HMEN_LAMPL to our cluster, and we start the next BLASTP search with this sequence, yielding the following result (excerpt):

Let us again consider all sequences having a probability lower than $10^{-30}$ we and find that except for HMEA_MYXGL, all sequences are contained in the cluster. This sequence is now included in the cluster, and the next BLASTP search is started with it. This search yields the following result (excerpts):

| Sequences found: | Probability: |
|---|---|
| SPR\|P31535\|HMEA_MYXGL HOMEOBOX PROTEIN ENGRAILED-LIKE A . . . | 3.8e-36 |
| SPR\|P31534\|HMEN_LAMPL HOMEOBOX PROTEIN ENGRAILED-LIKE (E . . . | 1.5e-30 |
| SPR\|P31538\|HMEB_XENLA HOMEOBOX PROTEIN ENGRAILED-1B (EN- . . . | 1.8e-30 |
| SPR\|P31537\|HMEA_XENLA HOMEOBOX PROTEIN ENGRAILED-1A (EN- . . . | 3.8e-30 |
| SPR\|P52729\|HMEC_XENLA HOMEOBOX PROTEIN ENGRAILED-2A (EN- . . . | 4.9e-29 |
| SPR\|P09015\|HME2_BRARE HOMEOBOX PROTEIN ENGRAILED-2 (ZF-E . . . | 1.4e-28 |
| SPR\|Q05925\|HME1_HUMAN HOMEOBOX PROTEIN ENGRAILED-1 (HU-E . . . | 1.7e-28 |
| SPR\|P09065\|HME1_MOUSE HOMEOBOX PROTEIN ENGRAILED-1 (MO-E . . . | 1.8e-28 |
| SPR\|P09066\|HME2_MOUSE HOMEOBOX PROTEIN ENGRAILED-2 (MO-E . . . | 3.1e-28 |
| SPR\|P19622\|HME2_HUMAN HOMEOBOX PROTEIN ENGRAILED-2 (HU-E . . . | 3.3e-28 |
| SPR\|Q05916\|HME1_CHICK HOMEOBOX PROTEIN ENGRAILED-1 (GG-E . . . | 4.6e-28 |
| SPR\|P52730\|HMED_XENLA HOMEOBOX PROTEIN ENGRAILED-2B (EN- . . . | 2.1e-27 |
| SPR\|Q05917\|HME2_CHICK HOMEOBOX PROTEIN ENGRAILED-2 (GG-E . . . | 2.2e-27 |
| SPR\|P09075\|HME6_APIME HOMEOBOX PROTEIN E60 (FRAGMENT). | 2.9e-27 |
| SPR\|P23397\|HMEN_HELTR HOMEOBOX PROTEIN HT-EN (FRAGMENT). | 4.4e-27 |
| SPR\|Q04896\|HME1_BRARE HOMEOBOX PROTEIN ENGRAILED-1. | 4.9e-27 |
| SPR\|P09076\|HME3_APIME HOMEOBOX PROTEIN E30 (FRAGMENT). | 5.4e-27 |
| SPR\|P31533\|HME3_BRARE HOMEOBOX PROTEIN ENGRAILED-3 (ZF-E . . . | 2.0e-26 |
| SPR\|P31536\|HMEB_MYXGL HOMEOBOX PROTEIN ENGRAILED-LIKE B . . . | 8.8e-26 |

| Sequences found: | Probability: |
|---|---|
| SPR\|P31534\|HMEN_LAMPL HOMEOBOX PROTEIN ENGRAILED-LIKE (E . . . | 5.7e-37 |
| SPR\|P31535\|HMEA_MYXGL HOMEOBOX PROTEIN ENGRAILED-LIKE A . . . | 5.0e-31 |
| SPR\|P31538\|HMEB_XENLA HOMEOBOX PROTEIN ENGRAILED-1B (EN- . . . | 1.4e-28 |
| SPR\|P31537\|HMEA_XENLA HOMEOBOX PROTEIN ENGRAILED-1A (EN- . . . | 2.9e-28 |
| SPR\|P23397\|HMEN_HELTR HOMEOBOX PROTEIN HT-EN (FRAGMENT). | 1.2e-27 |
| SPR\|P31536\|HMEB_MYXGL HOMEOBOX PROTEIN ENGRAILED-LIKE B . . . | 1.4e-27 |
| SPR\|Q04896\|HME1_BRARE HOMEOBOX PROTEIN ENGRAILED-1. | 1.5e-27 |
| SPR\|P09015\|HME2_BRARE HOMEOBOX PROTEIN ENGRAILED-2 (ZF-E . . . | 6.9e-27 |
| SPR\|Q05925\|HME1_HUMAN HOMEOBOX PROTEIN ENGRAILED-1 (HU-E . . . | 1.5e-26 |
| SPR\|P09065\|HME1_MOUSE HOMEOBOX PROTEIN ENGRAILED-1 (MO-E . . . | 1.6e-26 |
| SPR\|P09075\|HME6_APIME HOMEOBOX PROTEIN E60 (FRAGMENT). | 1.9e-26 |
| SPR\|Q05916\|HME1_CHICK HOMEOBOX PROTEIN ENGRAILED-1 (GG-E . . . | 4.5e-26 |

Above the threshold, we do not find any sequences that would not already be contained in our cluster, so the SYSTERS search for this inquiry sequence is now concluded, and the cluster contains the following 26 sequences:

| | | | | |
|---|---|---|---|---|
| HME1_HUMAN, | HME1_MOUSE, | HME1_CHICK, | HME2_CHICK, | HME2_HUMAn, |
| HME2_MOUSE, | HME2_BRARE, | HMEB_XENLA, | HMEC_XENLA, | HMED_XENLA, |
| HME3_BRARE, | HME1_BRARE, | HMEN_DROVI, | HMIN_DROME, | HMEN_BOMMO, |
| HMEN_DROME, | HMIN_BOMMO, | HMEN_TRIGR, | HMEN_ARTSF, | HME3_APIME, |
| HME6_APIME, | HMEN_SCHAM, | HMEN_HELTR, | HMEA_XENLA, | HMEA_MYXGL, |
| HMEN_LAMPL. | | | | |

If this procedure is performed for all 28 sequences annotated as homeobox engrailed in the Swissprot database, this yields 28 clusters at first. The clusters thus found are plotted in the following table against the sequences, where the columns represent the clusters belonging to the inquiry sequence listed at the head of the table and the line indicate the clusters in which the sequence listed at the left is contained (marked with an X). In this case, there are seven clusters having 27 sequences each, five clusters having 26 sequences each, etc.

| Sequence | Cluster (inquiry sequence) | | | | | | | |
|---|---|---|---|---|---|---|---|---|
| | 1 (HME2_BRARE) | 2 (HME2_MOUSE) | 3 (HMEB_XENLA) | 4 (HMEC_XENLA) | 5 (HMED_XENLA) | 6 (HMEN_LAMPL) | 7 (HMEA_MYXGL) | 8 (HMEA_XENLA) |
| HME2_BRARE |   | X | X | X | X | X | X | X |
| HME2_MOUSE | X |   | X | X | X | X | X | X |
| HMEB_XENLA | X | X |   | X | X | X | X | X |
| HMEC_XENLA | X | X | X |   | X | X | X | X |
| HMED_XENLA | X | X | X | X |   | X | X | X |
| HMEN_LAMPL | X | X | X | X | X |   | X |   |
| HMEA_MYXGL | X | X | X | X | X | X |   | X |
| HMEA_XENLA | X | X | X | X | X | X | X |   |
| HM16_CAEEL | X | X | X | X | X | X | X | X |
| HME1_MOUSE | X | X | X | X | X | X | X | X |
| HMEN_DROME | X | X | X | X | X | X | X | X |
| HMIN_DROME | X | X | X | X | X | X | X | X |
| HME6_APIME | X | X | X | X | X | X | X | X |
| HME3_APIME | X | X | X | X | X | X | X | X |
| HMEN_DROVI | X | X | X | X | X | X | X | X |
| HMEN_TRIGR | X | X | X | X | X | X | X | X |
| HMEN_SCHAM | X | X | X | X | X | X | X | X |
| HMEN_HELTR | X | X | X | X | X | X | X | X |
| HMEN_BOMMO | X | X | X | X | X | X | X | X |
| HME3_BRARE | X | X | X | X | X | X | X | X |
| HME1_BRARE | X | X | X | X | X | X | X | X |
| HMIN_BOMMO | X | X | X | X | X | X | X | X |
| HMEN_ARTSF | X | X | X | X | X | X | X | X |
| HME2_HUMAN | X | X | X | X | X | X | X | X |
| HME1_CHICK | X | X | X | X | X | X | X | X |
| HME2_CHICK | X | X | X | X | X | X | X | X |
| HME1_HUMAN | X | X | X | X | X | X | X | X |
| HMEB_MYXGL | X | X | X | X | X | X | X | X |

| Sequence | Cluster (inquiry sequence) | | | | | | | |
|---|---|---|---|---|---|---|---|---|
| | 9 (HM16_CAEEL) | 10 (HME1_MOUSE) | 11 (HMEN_DROME) | 12 (HMIN_DROME) | 13 (HME6_APIME) | 14 (HME3_APIME) | 15 (HMEN_DROVI) | 16 (HMEN_TRIGR) |
| HME2_BRARE | X | X | X | X | X | X | X | X |
| HME2_MOUSE | X | X | X | X | X | X | X | X |
| HMEB_XENLA | X | X | X | X | X | X | X | X |
| HMEC_XENLA | X | X | X | X | X | X | X | X |
| HMED_XENLA | X | X | X | X | X | X | X | X |
| HMEN_LAMPL | X |   | X | X | X | X |   |   |
| HMEA_MYXGL |   | X |   |   |   |   |   |   |
| HMEA_XENLA | X | X | X | X | X | X | X | X |
| HM16_CAEEL |   | X | X | X | X | X | X | X |
| HME1_MOUSE | X |   | X | X | X | X | X | X |
| HMEN_DROME | X | X |   | X | X | X | X | X |
| HMIN_DROME | X | X | X |   | X | X | X | X |
| HME6_APIME | X | X | X | X |   | X | X | X |
| HME3_APIME | X | X | X | X | X |   | X | X |

-continued

| Sequence | 17 (HMEN_SCHAM) | 18 (HMEN_HELTR) | 19 (HMEN_BOMMO) | 20 (HME3_BRARE) | 21 (HME1_BRARE) | 22 (HMIN_BOMMO) | 23 (HMEN_ARTSF) |
|---|---|---|---|---|---|---|---|
| HMEN_DROVI | X | X | X | X | X | X | X |
| HMEN_TRIGR | X | X | X | X | X | X | X |
| HMEN_SCHAM | X | X | X | X | X | X | X |
| HMEN_HELTR | X | X | X | X | X | X | X |
| HMEN_BOMMO | X | X | X | X | X | X | X |
| HME3_BRARE | X | X | X | X | X | X | X |
| HME1_BRARE | X | X | X | X | X | X | X |
| HMIN_BOMMO | X | X | X | X | X | X | X |
| HMEN_ARTSF | X | X | X | X | X | X | X |
| HME2_HUMAN | X | X | X | X | X | X | X |
| HME1_CHICK | X | X | X | X | X | X | X |
| HME2_CHICK | X | X | X | X | X | X | X |
| HME1_HUMAN | X | X | X | X | X | X | X |
| HMEB_MYXGL | X | X | X | X | X | X | X |

Cluster (inquiry sequence)

| Sequence | 17 (HMEN_SCHAM) | 18 (HMEN_HELTR) | 19 (HMEN_BOMMO) | 20 (HME3_BRARE) | 21 (HME1_BRARE) | 22 (HMIN_BOMMO) | 23 (HMEN_ARTSF) |
|---|---|---|---|---|---|---|---|
| HME2_BRARE | X | X | X | X | X | X | X |
| HME2_MOUSE | X | X | X | X | X | X | X |
| HMEB_XENLA | X | X | X | X | X | X | X |
| HMEC_XENLA | X | X | X | X | X | X | X |
| HMED_XENLA | X | X | X | X | X | X | X |
| HMEA_MYXGL |   |   |   |   |   |   |   |
| HMEA_XENLA | X | X |   | X | X | X | X |
| HM16_CAEEL | X | X | X | X | X | X | X |
| HME1_MOUSE | X | X | X | X | X | X | X |
| HMEN_DROME | X | X | X | X | X | X | X |
| HMIN_DROME | X | X | X | X | X | X | X |
| HME6_APIME | X | X | X | X | X | X | X |
| HME3_APIME | X | X | X | X | X | X | X |
| HMEN_DROVI | X | X | X | X | X | X | X |
| HMEN_TRIGR | X | X | X | X | X | X | X |
| HMEN_SCHAM | X | X | X | X | X | X | X |
| HMEN_HELTR | X | X | X | X | X | X | X |
| HMEN_BOMMO | X | X | X | X |   | X | X |
| HME3_BRARE | X | X | X | X | X | X | X |
| HME1_BRARE | X | X | X | X | X | X | X |
| HMIN_BOMMO | X | X | X | X | X | X | X |
| HMEN_ARTSF | X | X | X | X | X | X | X |
| HME2_HUMAN | X | X | X | X | X | X | X |
| HME1_CHICK | X | X | X | X | X | X | X |
| HME2_CHICK | X | X | X | X | X | X | X |
| HME1_HUMAN | X | X | X | X | X | X | X |
| HMEB_MYXGL | X | X | X | X | X | X | X |

-continued

| Sequence | 24 (HME2_HUMAN) | 25 (HME1_CHICK) | 26 (HME2_CHICK) | 27 (HME1_HUMAN) | 28 (HMEB_MYXGL) |
|---|---|---|---|---|---|
| | | | Cluster (inquiry sequence) | | |
| HME2_BRARE | X | X | X | X | |
| HME2_MOUSE | X | X | X | X | |
| HMEB_XENLA | X | X | X | X | |
| HMEC_XENLA | X | X | X | X | |
| HMED_XENLA | X | X | X | X | |
| HMEN_LAMPL | X | X | X | X | |
| HMEA_MYXGL | X | X | X | X | |
| HMEA_XENLA | X | X | X | X | |
| HM16_CAEEL | | | | | |
| HME1_MOUSE | X | X | X | X | |
| HMEN_DROME | X | X | X | X | |
| HMIN_DROME | X | X | X | X | |
| HME6_APIME | X | X | X | X | |
| HME3_APIME | X | X | X | X | |
| HMEN_DROVI | X | X | X | X | |
| HMEN_TRIGR | X | X | X | X | |
| HMEN_SCHAM | X | X | X | X | |
| HMEN_HELTR | X | X | X | X | |
| HMEN_BOMMO | X | X | X | X | |
| HME3_BRARE | X | X | X | X | |
| HME1_BRARE | X | X | X | X | |
| HMIN_BOMMO | X | X | X | X | |
| HMEN_ARTSF | X | X | X | X | |
| HME2_HUMAN | X | X | X | X | |
| HME1_CHICK | X | X | X | X | |
| HME2_CHICK | X | X | X | X | |
| HME1_HUMAN | X | X | X | X | |
| HMEB_MYXGL | | | | | X |

After removing identical clusters and solving for inclusions, the homeobox engrailed proteins are distributed among two clusters—one with 27 sequences and the other with only the HMEA_MYXGL sequence.

What is claimed is:

1. A method of grouping sequences in a sequence database to provide a sequence cluster containing similar sequences, the method comprising:

(a) providing an inquiry sequence;

(b) determining a positive quantity of similar sequences to said inquiry sequence from the sequence database using a database search program, wherein said positive quantity of similar sequences includes all sequences in said sequence database for which the probability that similarity occurs randomly is below a predetermined threshold level;

(c) selecting one sequence having the highest probability of randomly occurred similarity from said positive quantity determined for said inquiry sequence as a subsequent search sequence;

(d) determining a subsequent positive quantity of similar sequences for said subsequent search sequence from the sequence database using the database search program as in (b);

(e) identifing new sequences in said subsequent positive quantity that are not included in said positive quantity determined for said inquiry sequence, said new sequences being combined with said positive quantity of similar sequences of said inquiry sequence;

(f) repeating steps (c) to (e) as long as new sequences are still identified that are not contained in the combined positive quantity of similar sequences of step (e) and as long as there is an intersection between sequences in the combined positive quantity and any sequences in the subsequent positive quantity; and (g) outputting all the different sequences contained in the combined positive quantity as one cluster containing similar sequences.

2. A method of clustering all sequences in a sequence database, according to the method of claim 1, further comprising:

(h) repeating steps (a)–(g) for each sequence in the sequence database to obtain multiple clusters, (i) removing clusters that occur more than once except for one cluster;

(j) removing clusters that are contained in other clusters, (j) of the remaining clusters, outputting those clusters that do not overlap with other clusters as partitioning of the database, and (k) outputting remaining overlapping clusters as groups whose clusters are linked together by overlapping.

3. The method of claim 1, wherein the threshold level of probability is between $10^{-20}$ and $10^{-35}$.

4. The method of claim 2, wherein the threshold level of probability is between $10^{-20}$ and $10^{-35}$.

* * * * *

UNITED STATES PATENT AND TRADEMARK OFFICE
CERTIFICATE OF CORRECTION

PATENT NO. : 6,304,868 B1 Page 1 of 1
DATED : October 16, 2001
INVENTOR(S) : Martin Vigron and Antje Krause It is certified that error appears in the above-identified patent and that said Letters Patent is hereby corrected as shown below:

Column 2,
Line 65, "end if" should not be indented

Signed and Sealed this

Seventeenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 6,304,868 B1
DATED : October 16, 2001
INVENTOR(S) : Martin Vigron and Antje Krause It is certified that error appears in the above-identified patent and that said Letters Patent is hereby corrected as shown below:

Column 10, Row HMEA_XENLA, Column HM16_CAEEL: "X" should be deleted
Column 10, Row HMEA_MYXGL, Column HME1_MOUSE: "X" should be deleted
Column 10, Row HMEA_XENLA, Column HMEN_DROME: "X" should be deleted
Column 10, Row HMEA_XENLA, Column HMIN_DROME: "X" should be deleted
Column 10, Row HMEA_XENLA, Column HME6_APIME: "X" should be deleted
Column 10, Row HMEA_XENLA, Column HME3_APIME: "X" should be deleted
Column 10, Row HMEA_XENLA, Column HMEN_DROVI: "X" should be deleted
Column 10, Row HMEA_XENLA, Column HMEN_TRIGR: "X" should be deleted
Column 10, Row HMEA_XENLA, Column HMEN_SCHAM: "X" should be deleted
Column 10, Row HMEA_XENLA, Column HMEN_HELTR: "X" should be deleted
Column 10, Row HMEA_XENLA, Column HMEN_BOMMO: "X" should be deleted
Column 10, Row HMEA_XENLA, Column HME3_BRARE: "X" should be deleted
Column 10, Row HMEA_XENLA, Column HME1_BRARE: "X" should be deleted
Column 10, Row HM16_CAEEL, Column HMIN_BOMMO: "X" should be deleted Signed and Sealed this First Day of April, 2003

JAMES E. ROGAN
*Director of the United States Patent and Trademark Office*